United States Patent [19]
Hobart et al.

[11] Patent Number: 5,891,718
[45] Date of Patent: Apr. 6, 1999

[54] TETRACYCLINE INDUCIBLE/REPRESSIBLE SYSTEMS

[75] Inventors: Peter M. Hobart, Poway; Xiaowu Liang, La Jolla, both of Calif.

[73] Assignee: Vical Incorporated, San Diego, Calif.

[21] Appl. No.: 622,956

[22] Filed: Mar. 27, 1996

[51] Int. Cl.⁶ .............. C12N 5/00; C12N 15/00; C07H 21/04
[52] U.S. Cl. .............. 435/325; 435/320.1; 536/24.1
[58] Field of Search .............. 514/44; 435/172.3, 435/240.2, 320.1; 424/199.1; 935/22, 33, 34; 536/24.1

[56] References Cited

U.S. PATENT DOCUMENTS

5,464,758  11/1995  Gossen et al. .

FOREIGN PATENT DOCUMENTS

| WO 90/11092 | 10/1990 | WIPO . |
|---|---|---|
| 94/04672 | 3/1994 | WIPO . |
| WO 94/29442 | 12/1994 | WIPO . |
| WO 96/40946 | 12/1996 | WIPO . |
| WO 97/00947 | 1/1997 | WIPO . |

OTHER PUBLICATIONS

Kim. H–J.. et al. (1995) Tetracycline Repressor–Regulated Gene Repression in Recombinant Human Cytomegalovirus. Journal of Virology 69(4):2565–2573.

Shockett, P.. et al. (1995) A modified tetracycline–regulated system provides autoregulatory, inducible gene expression in cultured cells and transgenic mice. Proc. Natl. Acad. Sci. 92:6522–6526.

Acsadi, G., et al. (1991) Human dystrophin expression in mdx mice after intramuscular injection of DNA constructs. Nature 352:815–818.

Chapman B., et al. (1991) Effect of intron A from human cytomegalovirus (Towne) immediate–early gene on heterologous expression in mammalian cells. Nucleic Acids Research 19(14):3979–3986.

Choi, T., et al. (1991) A generic intron increases gene expression in transgenic mice. Molecular and Cellular Biology 11(6):3070–3074.

Conry, R., et al. (1995) A carcinoembryonic antigen polynucleotide vaccine has in vivo antitumor activity. Gene Therapy 2:59–65.

Davis, H., et al. (1993) DNA–based immunization induces continuous secretion of hepatitis B surface antigen and high levels of circulating antibody. Human Molecular Genetice 2(11):1847–1851.

Deuschle, U., et al. (1995) Tetracycline–reversible silencing of eukaryotic promoters. Molecular and Cellular Biology 15(4):1907–1914.

Elory–Stein, O., et al. (1989) Cap–independent translation of mRNA conferred by encephalomyocarditis virus 5' sequence improves the performance of the vaccinia virus/bacteriophage T7 hybrid expression system. Proc. Natl Acad. Sci. 86:6126–6130.

Felgner, P., et al. (1991) The direct delivery of purified genes in vivo and their application as drugs, without the use of retroviruses, is discussed. Gene therapeutics 349:351–352.

Felgner, J., et al. (1994) Enhanced gene delivery and mechanism studies with a novel series of cationic lipid formulations. The Journal of Biological Chemistry 269:2550–2561.

Fishman, G., et al. (1994) Tetracycline–regulated cardiac gene expression in vivo. J. Clin. Invest. 93:1864–1868.

Furth, P., et al. (1994) Temporal control of gene expression in transgenic mice by a tetracycline–responsive promoter. Proc. Natl. Acad. Sci. 91:9302–9306.

(List continued on next page.)

Primary Examiner—Bruce R. Campell
Assistant Examiner—Abdur Razzaque
Attorney, Agent, or Firm—Knobbe, Martens, Olson & Bear, LLP.

[57] ABSTRACT

This application relates to effector controlled eukaryotic expression vectors adapted for use in gene therapy or gene immunization having positive feedback regulation.

16 Claims, 7 Drawing Sheets

OTHER PUBLICATIONS

Gatz, C., et al. (1992) Stringent repression and homogeneous de–repression by tetracycline of a modified CaMV 35S promoter in intact transgenic tobacco plants. The Plant Journal 2(3);397–404.

Gossen, M., et al. (1993) Control of gene activity in higher eukaryotic cells by prokaryotic regulatory elements. TIBS 471–475.

Gossen, M., et al. (1995) Transcriptional activation by tetracyclines in mammalian cells. Science 268:1766–1769.

Gossen, M., et al. (1992) Tight control of gene expression in mammalian cells by tetracycline–responsive promoters. 89:5547–5551.

Hawkins, R., et al. (1993) A genetic approach to idiotypic vaccination. Journal of Immunotherapy 14:273–278.

Hinrichs, W., et al. (1994) Structure of the tet repressor–tetracycline complex and regulation of antibiotic resistance. Science 264:418–420.

Horn N., et al. (1995) Cancer gene therapy using plasmid DNA: purification of DNA for human clinical trials. Human Gene Therapy 6:565–573.

Jans, D., et al. (1994) Negative charge at the casein kinase II site flanking the nuclear localization signal of the SV40 large T–antigen is mechanistically important for enhanced nuclear import. Oncogene 9:2961–2968.

Kalderon, D., et al. (1984) A short amino acid sequence able to specify nuclear location. Cell 39:499–509.

Lew, D., et al. (1995) Cancer gene therapy using plasmid DNA: pharmacokinetic study of DNA following injection in mice. Human Gene Therapy 6:553–564.

Manthorpe, M., et al. (1993) Gene therapy by intramuscular injection of plasmid DNA: studies on firefly luciferase gene expression in mice. Human Gene Therapy 4:419–431.

Morgan, R., et al. (1992) Retroviral vectors containing putative internal ribosome entry sites: development of a polycistronic gene transfer system and applications to human gene therapy. Nucleic Acids Research 20(6):1293–1299.

Nabel, G., et al. (1993) Direct gene transfer with DNA–liposome complexes in melanoma: expression, biologic activity, and lack of toxicity in humans. Proc. Natl. Acad. Sci. 90:11307–11311.

Parker, S., et al. (1995) Cancer gene therapy using plasmid DNA: safety evaluation in rodents and non–human primates. Human Gene Terapy 6:575–590.

Perales, J., et al. (1994) Gene transfer in vivo: sustained expression and regulation of genes introduced into the liver by receptor–targeted uptake. Proc. Natl. Acad. Sci. 91:4086–4090.

Pescini, R., et al. Regulatable gene activation/inhibition using a powerful genetic switch. Technology Advances for Gene Therapy.

Sankaran, L., et al. (1992) A simple quantitative assay for chloramphenicol acetyltransferase by direct extraction of the labeled product into scintillation cocktail. Analytical Biochemistry 200:180–186.

Sedegah, M., et al. (1994) Protection against malaria by immunization with plasmid DNA encoding circumsporozoite protein. Proc. Natl. Acad. Sci. 91:9866–9870.

Ulmer, J., et al. (1993) Heterologous protection against influenza by injection of DNA encoding a viral protein. Science 259:1745–1749.

Wolff, J., et al. (1990) Direct gene transfer into mouse muscle in vivo. Science 247:1465–1468.

Yoshimura., K., et al. (1992) Expression of the human cystic fibrosis transmembrane conductance regulator gene in the mouse lung after in vivo intratracheal plasmid–mediated gene transfer. Nucleic Acids Research 20(12):3233–3240.

Chen, X., et al. (1994) A self–initiating eukaryotic transient gene expression system based on cotransfection of bacteriophage T7 RNA polymerase and DNA vectors containing a T7 autogene. Nucleic Acids Research 22(11):2114–2120.

E. Marshall (1995) Science 269:1050–1055.

N. Miller et al (1995) Targeted Gene Therapy 9:190–199.

Bidirectional CWV IE Enhancer/Promoter Control Element

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

```
GTACGGCACC  CAAGAAGAAG  CGGAAGGTCC  CAGGTGTACC  GAGCTCGAAT  TGCG                    5 4
```

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:2:

```
Lys  Lys  Lys  Arg  Lys
 1                   5
```

TETRACYCLINE INDUCIBLE/REPRESSIBLE SYSTEMS

FIELD OF THE INVENTION

This application relates to effector controlled eukaryotic expression vectors adapted for use in gene therapy or gene immunization having positive feedback regulation.

BACKGROUND OF THE INVENTION

PCT/US90/01515 describes products and processes for gene therapy and gene immunization by direct introduction of naked or lipid-complexed polynucleotides into body tissue of a host vertebrate. (All references cited hereunder are incorporated herein by reference.) The naked polynucleotides are naked in the sense that they are free of certain indicated additives, such as transfection-facilitating proteins, viral particles, liposomes, charged lipids, and calcium phosphate precipitating agents. The lipid-complexed polynucleotides are formed of polynucleotides and lipids.

PCT/US94/06734 describes the work by Gossen, M. & Bujard, H. *Proc Natl Acad Sci USA* 89, 5547–5551 (1992). See also Gossen, M., Bonin, A. L. & Bujard, H. *TIBS* 18, 471–475 (1993). (All references cited hereunder are incorporated herein by reference.) Gossen and Bujard adapted a prokaryotic tetracycline system to produce a genetic switch for achieving control of eukaryotic gene expression. In the native prokaryotic tetracycline system, tetracycline is an effector that induces prokaryotic gene expression. Tetracycline accomplishes this by binding to a tetracycline repressor protein. In the absence of tetracycline, the tetracycline repressor binds a tetracycline operator sequence, which is linked to a promoter, and represses transcription. In the presence of tetracycline, the tetracycline repressor binds tetracycline, which binding displaces the repressor from the tetracycline operator sequence, so repression is relieved and transcription can begin.

The Gossen and Bujard adaptation, instead of being a tetracycline repressor system, is a tetracycline activator system. In this system, a tetracycline-controlled activator protein is prepared by fusing the tetracycline repressor to a transcription activation domain from another protein that activates transcription in eukaryotic cells, causing the resultant chimeric protein to retain the repressor's binding capabilities, while also possessing the property of activating transcription in eukaryotic cells. In the absence of tetracycline, the tetracycline-controlled activator binds the tetracycline operator sequence, which is linked to a promoter, and activates transcription. In the presence of tetracycline, the tetracycline-controlled activator binds tetracycline, which binding displaces the activator from the tetracycline operator sequence, so activation is ended and transcription is silenced.

According to Furth, P. A., et al. *Proc Natl Acad Sci USA* 91, 9302–9306 (1994), the Gossen and Bujard group generated a transgenic mouse based on the tetracycline activator system. In Gatz, C., Frohberg, C. & Wendenburg, R. *Plant J* 2, 397–404 (1992), this investigative group produced a transgenic plant using the tetracycline repressor system. Each regulatory system exploits the prokaryotic tetracycline mechanism as a genetic switch to turn genes on and off.

These regulatory systems require that two different kinds of expression vectors enter each transfected cell. For example, in the tetracycline activator system, a first expression vector is necessary that encodes the tetracycline-controlled activator. A second expression vector is required that encodes the gene of interest placed under the control of the tetracycline operator sequence linked to a promoter.

Similarly, in the tetracycline repressor system, the tetracycline repressor is encoded by one expression vector. The gene of interest is encoded by another expression vector placed under the control of the tetracycline operator sequence linked to a promoter.

Such two-vector systems are, however, problematic. The probability of transfecting a single cell with two plasmid DNAs is significantly lower than for transfecting that cell with one plasmid DNA. Moreover, the transfection efficiencies for different kinds of plasmid DNAs may vary dramatically. Furthermore, even where multiple copies of plasmid DNA get transfected into cells, the sheer number of plasmid DNAs is presumed to affect the level of expression, making it important for regulation of that expression to have both kinds of plasmid DNAs available in sufficiently representative quantities.

PCT/US94/06734 tried to solve the two-vector problem by eliminating the need to encode one of the genes, to wit, the gene of interest. A DNA construct was designed for homologous recombination at a single site in a haploid genome. This construct encoded only the tetracycline-controlled activator and placed the tetracycline operator sequence linked to a promoter in a position so that, upon successful integration, it controlled the expression of an endogenous gene. Successful integration was also intended to position the sequence encoding the tetracycline-controlled activator under the control of the promoter of that endogenous gene.

This single construct system served the purpose of generating a conditional gene knockout. Functioning as a single copy, in an integrated state, at a predetermined locus, this plasmid was not developed to shuttle individual genes into cells, in contrast to gene therapy and gene immunization described in PCT/US90/01515 where plasmids are present as multiples copies, in episomal form, and for the express purpose of gene delivery. Additionally, this single plasmid solution was limited to the production of organisms as "transgenics," given the technical manipulations required to bring about homologous recombination, thus effectively precluding its usefulness in gene therapy and gene immunization in humans.

Even this single construct solution fails to overcome additional existing difficulties. It is critical that expression not be leaky in these regulatory systems that seek to control gene activity. To ensure this, PCT/US94/06734 contemplated insulating one transcription unit, constituting the endogenous gene and the tetracycline response element, from the other transcription unit, having the sequence encoding the tetracycline-controlled activator under the control of the endogenous promoter. For example, strong transcription terminators were envisioned for placement between these transcription units.

Now that individual genes can be administered as drugs and vaccines for use in gene therapy and gene immunization, there arises an urgent and compelling need to provide delivery of these genes and regulate expression of their gene products. The realization of this goal through the development of regulatory systems should take into account the problems of two-plasmid systems. It would be particularly beneficial if any such regulatory systems could address the issue of leaky gene expression toward achieving genetic control.

Accordingly, it is an objective of the invention to provide effector controlled eukaryotic expression vectors adapted for use in gene therapy and gene immunization.

It is another objective of the invention to provide these vectors as single vector constructs that contain all the elements necessary for a regulatory system on a single construct.

It is yet another objective of the invention to provide such vectors as having positive feedback regulation.

These and other objectives of the invention will be apparent upon consideration of the specification as a whole.

SUMMARY OF THE INVENTION

According to one aspect of the invention there is provided a self-accelerating eukaryotic expression vector adapted for use in gene therapy or gene immunization comprising a single transcription unit under the control of an activator-responsive promoter, the activator being itself controlled by an effector, and the unit comprising a first cistron encoding a desired gene product and a second cistron encoding the activator, and an internal ribosome entry site positioned between the cistrons. The promoter may comprise a minimal promoter linked to an operator sequence. The minimal promoter may be derived from a cytomegalovirus immediate early gene promoter. The operator sequence may be a tetracycline operator sequence. The activator may be a tetracycline-controlled activator. The tetracycline-controlled activator may comprise a tetracycline repressor fused to a transcription activation domain that activates transcription in eukaryotic cells. The tetracycline-controlled activator may comprise a tetracycline repressor fused to a transcription activation domain that activates transcription in eukaryotic cells and further fused to a nuclear localization signal. The transcription activation domain may be derived from herpes simplex virus virion protein 16. The nuclear localization signal may be derived from SV40 large T antigen. The first cistron may be positioned 5-prime of the second cistron within the transcription unit.

According to another aspect of the invention there is provided a self-accelerating eukaryotic expression vector adapted for use in gene therapy or gene immunization comprising a single transcription unit under the control of a tetracycline-controlled activator-responsive promoter, the unit comprising a first cistron encoding a desired gene product and a second cistron encoding the tetracycline-controlled activator, and an internal ribosome entry site positioned between the cistrons. The promoter may comprise a minimal promoter linked to a tetracycline operator sequence. The minimal promoter may be derived from a cytomegalovirus immediate early gene promoter. The tetracycline- controlled activator may comprise a tetracycline repressor fused to a transcription activation domain that activates transcription in eukaryotic cells. The tetracycline-controlled activator may comprise a tetracycline repressor fused to a transcription activation domain that activates transcription in eukaryotic cells and further fused to a nuclear localization signal. The transcription activation domain may be derived from herpes simplex virus virion protein 16. The nuclear localization signal may be derived from SV40 large T antigen. The first cistron may be positioned 5-prime of the second cistron within the transcription unit.

According to yet another aspect of the invention there is provided a host cell comprising any of these eukaryotic expression vectors.

Based on another aspect of the invention there is provided a process for producing any of these eukaryotic expression vectors comprising constructing a single transcription unit and operably linking it to an activator-responsive promoter in a plasmid backbone, the unit comprising a first cistron encoding a desired gene product and a second cistron encoding the activator, and an internal ribosome entry site positioned between the cistrons; and isolating the resultant plasmid.

Based on yet another aspect of the invention there is provided a process for producing any of these eukaryotic expression vectors comprising constructing a single transcription unit and operably linking it to a tetracycline-controlled activator-responsive promoter in a plasmid backbone, the unit comprising a first cistron encoding a desired gene product and a second cistron encoding the tetracycline-controlled activator, and an internal ribosome entry site positioned between the cistrons; and isolating the resultant plasmid.

The invention also provides a process for inhibiting expression of the gene product in any of the host cells of above comprising contacting the cell with tetracycline or a tetracycline analog.

The invention further provides a vaccine comprising any of the eukaryotic expression vectors of above in a physiologically-acceptable carrier, where the gene product is an immunogen that stimulates a protective immune response in a host vertebrate.

The invention additionally provides a drug comprising any of the eukaryotic expression vectors of above in a physiologically-acceptable carrier where the gene product is a molecule that induces a desired therapeutic effect in a host vertebrate. The gene product may be selected from the group consisting of interleukin-2, tumor necrosis factor, interferon, nerve growth factor, epidermal growth factor, human growth hormone, LDL receptor, tissue plasminogen activator, Factor VII, Factor IX, granulocyte-macrophage colony-stimulating factor, erythropoietin, insulin, calcitonin, thymidine kinase, dystrophin, and CFTR.

In another aspect, the invention provides a composition of matter comprising a eukaryotic expression vector having the identifying characteristics of ATCC 97467.

In a further aspect, the invention provides a composition of matter comprising a eukaryotic expression vector having the identifying characteristics of ATCC 97467, where the CAT encoding sequence is replaced by a sequence encoding a protein of interest.

DETAILED DESCRIPTION OF THE PREFERRED EMBODIMENT

Figure 1A:
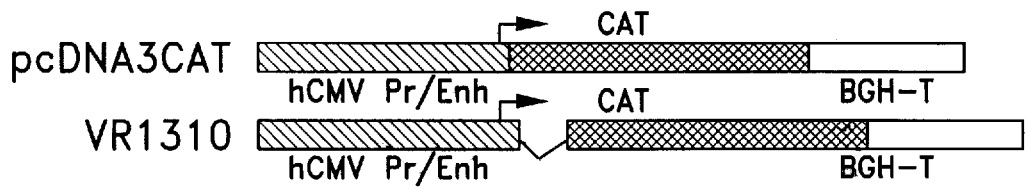
FIGS. 1A–1D. Plasmid constructs. A, human cytomegalovirus immediate-early gene promoter/enhancer based reporter constructs. Arrows indicate transcriptional start site and direction. The intron A from hCMV-IE is shown as a bent line. BGH-T indicates a transcription terminator from the bovine growth hormone gene. B, tTA/tetracycline-regulatable reporter constructs. Vectors VR1312 and VR1250 are based on a chimeric promoter containing 7 repeats of tetracycline operator sequences and hCMV-IE gene minimal promoter plus intron A. In plasmid VR1340, 4 copies of tetracycline operator sequences are located immediately downstream from the TATA box of hCMV-IE promoter/enhancer. C, tTA constructs. VR1502 is derived from pUHD15-1 by inserting a nuclear localization signal (NLS) from SV40 large T antigen in frame between tetR and VP16. D, bicistronic single plasmid construct. The CAP Independent Translation Enhancer (CITE) sequence was placed between the coding regions for CAT and tTA-NL.

Now that individual genes can be administered as drugs and vaccines for use in gene therapy and gene immunization, the regulatory systems of the present invention fulfill an urgent and compelling need to provide delivery of these genes and regulate expression of their gene products. These regulatory systems solve the problems of two-plasmid systems. They also overcome the difficulties of leaky gene expression for achieving genetic control.

Accordingly, the invention provides effector controlled eukaryotic expression vectors adapted for use in gene therapy and gene immunization.

The invention also provides these vectors as single vector constructs that contain all the elements necessary for a regulatory system on a single construct.

The invention further provides such vectors as having positive feedback regulation.

Regulatory Systems

The regulatory systems employed in this invention are based upon at least two important components: a gene regulatory protein, which turns the gene it regulates on or off; and an operator, which is a DNA sequence that the gene regulatory protein binds to initiate or inhibit transcription.

Regulatory systems are found in both prokaryotes and eukaryotes, and adaptation of either to eukaryotic expression vectors is contemplated. Regulatory systems in prokaryotes are simple, and preferred. They are especially preferred because their adaptation to eukaryotic expression vectors more readily circumvents pleiotropic effects.

In prokaryotes, gene regulatory proteins control transcription through either positive or negative regulation. In negative regulation, the gene regulatory protein is usually a repressor protein. Binding of this repressor to the operator DNA sequence typically prevents the binding of an RNA polymerase to the promoter of the relevant gene and consequently blocks initiation of transcription. The addition of an effector molecule switches the gene on when the effector is an inducing ligand, because the effector binds the repressor causing it to release the operator and thus allows transcription to proceed.

Alternatively, in positive regulation, the gene regulatory protein is often an activator protein. Binding of this activator to the operator DNA sequence commonly facilitates the binding of an RNA polymerase to the promoter of the particular gene and consequently activates initiation of transcription. The addition of an effector molecule switches the gene off if the effector is an inhibitory ligand, because the effector binds the activator causing it to release the operator and hence prohibits transcription from proceeding.

The present invention contemplates both positive and negative regulatory systems, and combinations of these. While positive regulatory systems are preferred, negative regulatory systems are not excluded. Establishing these systems, whether as positive regulatory systems, negative regulatory systems, or combinations of these, on single vector constructs is expressly envisioned.

A Tetracycline-Controlled Activator And A Promoter Responsive To It

In one embodiment of the invention, the regulatory system of the invention combines a tetracycline-controlled activator and a promoter that is responsive to it. This tetracycline-controlled activator is a gene regulatory protein. Furthermore, for the promoter to be responsive to this activator, it possesses the appropriate tetracycline operator sequence, which is the DNA sequence to which the tetracycline-controlled activator binds to modulate gene transcription.

In this embodiment, the tetracycline-controlled activator comprises, for example, a chimeric protein constructed by fusing the tetracycline repressor protein to a transcription activation domain that activates transcription in eukaryotic cells.

The tetracycline repressor of this tetracycline-controlled activator is any prokaryotic protein that binds a tetracycline operator sequence in the absence but not the presence of tetracycline. It may be of any class type. It is, preferably, a Tn10-derived *E. coli* tetracycline repressor protein. This protein can be modified, however, in any way so long as the tetracycline-controlled activator that it comprises maintains the ability to bind a tetracycline operator sequence in the absence but not the presence of tetracycline.

The transcription activation domain of this tetracycline-controlled activator can operate either directly or indirectly to activate gene transcription. This domain includes that originating from any of various helix-turn-helix proteins, and, also, zinc finger proteins, leucine zipper proteins, and helix-loop-helix proteins. Alternatively, this domain can be a dimerization domain that dimerizes with other gene regulatory proteins, like zinc finger proteins, leucine zipper proteins, or helix-loop-helix proteins. The preferred transcription activation domain is derived from a virion protein 16 (VP16) of herpes simplex virus (HSV). This domain is preferably positioned at the carboxyl terminus of the tetracycline repressor domain in the chimeric protein that it comprises, but its position at the amino terminus, or internally, is not excluded, so long as the tetracycline-controlled activator retains its property of binding a tetracycline operator sequence and activating gene transcription.

The tetracycline-controlled activator optionally includes one or more additional amino acid sequences. For example, it can include a nuclear localization signal that favors localization of proteins to the nucleus of the cell. Any nuclear localization signal is suitable so long as it has the effect of engendering transport of the chimeric protein that it comprises to eukaryotic cell nuclei. The nuclear localization signal is, preferably, derived from a SV40 large T antigen. This signal is preferably positioned as a linker between the tetracycline repressor domain and the transcription activation domain in the tetracycline-controlled activator, but its location is dictated by its function of localizing the transacting factor to the eukaryotic cell nucleus without interfering with the activities of the other domains in the parent protein, such as binding a tetracycline operator sequence and activating gene transcription.

In this embodiment, the promoter responsive to the tetracycline-controlled activator comprises, for example, a hybrid DNA sequence having a minimal promoter linked to a tetracycline operator sequence.

At least one tetracycline operator sequence, advantageously 3 or 4 to 10, and preferably 7, is positioned in operable linkage with (and preferably 5-prime of) the minimal promoter. This tetracycline operator sequence is a DNA sequence that binds a tetracycline repressor protein in the absence but not the presence of tetracycline. It may respond to any class type. It is, preferably, derived from a tetracycline resistance operon encoded in Tn10 of *E. coli*. Its modification, however, is permitted in any way so long as the hybrid DNA sequence that it comprises possesses the ability to bind a tetracycline repressor protein in the absence and not the presence of tetracycline, and to mediate gene transcription upon the binding of activators like the tetracycline-controlled activator to the subject tetracycline operator properly positioned in operable linkage with the minimal promoter.

The minimal promoter is any promoter sequence (e.g., a TATA box) that defines the transcription start site but is itself incapable of initiating transcription efficiently. It is selected on the basis of its ability to initiate gene transcription upon the binding of activators such as the tetracycline-controlled activator to operably linked tetracycline repressor-binding sites. This minimal promoter is, preferably, derived from a human cytomegalovirus immediate early (hCMV-IE) virus gene promoter, but any partial promoter sequence will suffice so long as it fulfills these selection criteria.

This regulatory system is sensitive to the addition of effector molecules, specifically inhibitory ligands, like tetracycline. Accordingly, tetracycline is contemplated as being useful in this invention. So also are tetracycline analogs. These are molecules that mimic the effects of tetracycline. Examples of tetracycline analogs include anhydrotetracycline, doxycycline, chlorotetracycline, epioxytetracycline, etc.

This is a positive regulation system. The tetracycline-controlled activator is a gene regulatory protein that behaves as an activator protein. Binding of this activator to the tetracycline operator is permitted because the tetracycline repressor (of which this chimeric protein is composed) has a high affinity for the operator sequence. Such binding results not in repression of gene transcription, but rather in its activation because of the presence of the transcription activation domain in this chimeric protein that is selected on the basis of its activation of gene transcription in eukaryotic cells. This transcription activation domain allows the tetracycline-controlled activator, once its binding to the tetracycline operator has been mediated by the tetracycline repressor, to facilitate binding of an RNA polymerase at the minimal promoter and consequently to activate initiation of transcription. The addition of tetracycline switches off the gene being regulated since it is an effector molecule that behaves as an inhibitory ligand, whereby the tetracycline binds the activator causing it to release the operator and hence prohibits transcription from proceeding. This system can accordingly be turned on or off in a binary fashion by the administration of the effector. It can also be adjusted in a continuous function by varying the concentration of the effector and thus the level of gene expression.

Positive Feedback Mechanism

The invention provides bi-cistronic expression vectors that locate all the elements of a gene regulatory system on single vector constructs. Thus, in an embodiment of this invention, bi-cistronic vector constructs are provided comprising a single transcription unit under the control of a tetracycline-controlled activator-responsive promoter, the transcription unit comprising a first cistron encoding a desired gene product and a second cistron encoding the tetracycline-controlled activator, and an internal ribosome entry site positioned between the cistrons. These bi-cistronic expression vectors are advantageous because, by locating all the elements of a gene regulatory system on single vector constructs, they circumvent the problems of two-plasmid systems.

They are additionally advantageous because they are configured to operate through an accelerating positive feedback mechanism. Suppose, for example, that the transcription unit described above, under the control of an activator-responsive promoter, is leaky. In this example, the activator will be synthesized and will bind the activator-responsive promoter. The consequence will be synthesis of more activator, additional binding of the activator-responsive promoter, and further synthesis of even more activator, in a self-accelerating, runaway fashion. The concentration of the desired gene product consequently increases to a high level. The bi-cistronic eukaryotic expression vectors of the present invention work in this way.

This invention therefore dramatically departs from PCT/US94/06734, and Gossen, M. & Bujard, H. *Proc Natl Acad Sci USA* 89, 5547–5551 (1992). The prior art actually teaches away from the present invention, in that the prior art considers the leakiness inherent to gene expression a problem and a limitation. Rather than acquiesce in this characterization, the present invention actually exploits this so-called problem and limitation and transforms it into an advantage and a valuable resource. Thus, a random and yet inevitable event, formerly considered a worst case scenario, has been cultivated and harnessed to initiate the synthesis of the gene regulatory protein, which then stimulates its own continued production as well as that of the desired gene product, in an accelerating positive feedback mechanism that is amenable to exquisite power and control.

Tetracycline Inducible/Repressible Systems

The tetracycline inducible/repressible systems of the invention offer an additionally sophisticated level of control over eukaryotic gene expression. For example, the same tetracycline-controlled activator that is used to activate gene expression can be exploited, instead, to repress it. Depending on the configuration of the tetracycline-controlled activator-responsive promoter, tetracycline can be employed as either an inducing ligand or an inhibitory ligand. By adjusting the position of the tetracycline operator sequence in relation to the TATA box, the resultant promoter can be modified to function in either positive or negative regulation by tetracycline.

The capability of activating or repressing transcription with the same tetracycline-controlled activator presents an additionally exciting feature of this activator. These gene regulatory proteins are not necessarily dedicated activators or repressors. They function, instead, within regulatory frameworks whose function depends on the final assembly of the individual components.

Accordingly, in another embodiment of the invention, the regulatory system of the invention combines the same tetracycline-controlled activator described above with a different promoter that is nevertheless responsive to this activator to instead repress gene expression.

Here, the tetracycline-controlled activator-responsive promoter features a hybrid DNA sequence comprising a eukaryotic promoter linked to a tetracycline operator sequence. At least one tetracycline operator sequence, advantageously 3 to 10, and preferably 4, or 7, is positioned in operable linkage with (and preferably 3-prime of) the eukaryotic promoter. It is arranged so that binding of the tetracycline-controlled activator to this operator precludes binding of an RNA polymerase at the promoter and thus bars initiation of transcription. The eukaryotic promoter is any promoter sequence that defines the transcription start site and is itself quite capable of initiating transcription efficiently, unless when in operable linkage with the tetracycline operator sequence this operator is bound by the tetracycline-controlled activator.

This is a negative regulation system, in which the tetracycline-controlled activator is acting as a repressor protein. Binding of this gene regulatory protein to the operator serves to prevent the binding of an RNA polymerase to the promoter of the gene being regulated and consequently blocks initiation of transcription. The addition of an effector molecule that is an inducing ligand like tetracycline switches the gene on, because the effector binds the gene regulatory protein causing it to release the operator and thus allows transcription to proceed.

These ligand-inducing systems enable a complementary approach to the ligand-inhibiting systems described herein and represent another advance provided by the present invention.

Small Molecule-Controlled Plasmids

Small molecule-controlled plasmids according to the invention are prepared. Standard procedures are used. Sambrook, J., Frisch, E. F. & Maniatis, T. "Molecular Cloning, A Laboratory Manual," 2nd Edition, Cold Spring Harbor Laboratory Press, Cold Spring Harbor, N.Y., 1989.

Toward this end, plasmids pUHD10-3, containing a tetracycline-controlled activator-responsive promoter, that is, a tetracycline operator sequence (7 repeats) linked to a hCMV-IE minimal promoter, and pUHD15-1, expressing a tetracycline-controlled activator, are purchased from the Center for Molecular Biology, University of Heidelberg. Gossen, M. & Bujard, H. *Proc Natl Acad Sci USA* 89, 5547–5551 (1992). Expression vector pcDNA3 is purchased from Invitrogen (San Diego, Calif.). Vectors pUHD10-3CAT and pcDNA3CAT (FIG. 1) are constructed by inserting a SalI-BamHI fragment containing chloramphenicol acetyltransferase (CAT) from pBS-CAT (Promega, Madison, Wis.) into SalI-BamHI-cut pUHD10-3 and pcDNA3, respectively. Plasmid VR1310 (FIG. 1) is constructed by inserting the same CAT fragment into a parental vector, VCL1 010, which is a modified derivative of p-CMVint-BL. Manthorpe, M., et al. *Hum Gene Ther* 4, 419–431 (1993). The modifications include removing the SV40 origin of replication, replacing the SV40 transcription terminator with the one from bovine growth hormone (BGH) gene, replacing the bacterial β-lactamase gene for ampicillin resistance with the gene encoding aminoglycoside 3'-phosphotransferase for kanamycin resistance from Tn903, and insertion of a multiple cloning site. Lew, D., et al *Hum Gene Ther* 6, 553–564 (1995). This plasmid also contains the hCMV-IE gene 5-prime untranslated region and intron A sequence. Chapman, B. S., Thayer, R. M., Vincent, K. A. & Haigwood, N. L. *Nucl Acids Res* 19, 3979–3986 (1991); Choi, T., Huang, M., Gorman, C. & Jaenisch, R. *Mol Cell Biol* 11, 3070–3074 (1991). Vector VR1312 (FIG. 1) is made by replacing the hCMV-IE promoter/enhancer (a AvrII/Klenow to SacII fragment) in VR1310 with a XhoI/Klenow to SacII segment containing the chimeric tetracycline operator sequence/hCMV-IE minimal promoter from pUHD10-3. Plasmid VR1250 (FIG. 1) is given the same backbone as VR1312 with the luciferase coding sequence replacing CAT. Manthorpe, M., et al. *Hum Gene Ther* 4, 419–431 (1993). VR1502 (FIG. 1) is made by inserting synthetic complementary DNA fragments (GTA CGG CAC CCA AGA AGA AGC GGA AGG TCC CAG GTG TAC CGA GCT CGA ATT GCG) (SEQ ID NO:1) encoding a nuclear localization signal (KKKRK) (SEQ ID NO:2) in frame between the tetracycline repressor and VP16 domains (SpeI site) of the tetracycline-controlled activator encoded by pUHD15-1. Jans, D. & Jans, P. *Oncogene* 9, 2961–2968 (1994); Deuschle, U., Meyer, & W., Thiesen, H-J. *Mol Cell Biol* 15, 1907–1914 (1995). To construct VR1340 (FIG. 1), complementary oligonucleotide sequences representing 4 repeats of the tetracycline operator sequence are synthesized and inserted into a SacII site 4 bp downstream from the hCMV-IE promoter/enhancer, that is, 3-prime of the TATA box, and 5-prime of the hCMV-IE untranslated region and intron A. (Gatz, C., Frohberg, C. & Wendenburg, R. *Plant J* 2, 397–404 (1992)) VR1370 (FIG. 1) is constructed by ligating three DNA fragments together. The first is a BamHI digested VR1312 vector DNA. This fragment provides a chimeric promoter containing 7 repeats of tetracycline operator sequences (7 repeats) and hCMV-IE gene minimal promoter plus intron A connected to a fragment encoding CAT. The second is the EcoR1 BamH1 fragment from VR1502. This second fragment provides the coding sequence for the tetracycline repressor/NL/VP16 fusion protein. The third is a PCR'd fragment from a commercially available plasmid pCITE (Novagen, Inc., Madison, Wis.)

using a 5-prime primer with a BglII restriction site and a 3-prime primer with a EcoRI restriction site.

In Vitro Testing

Figure 2A:
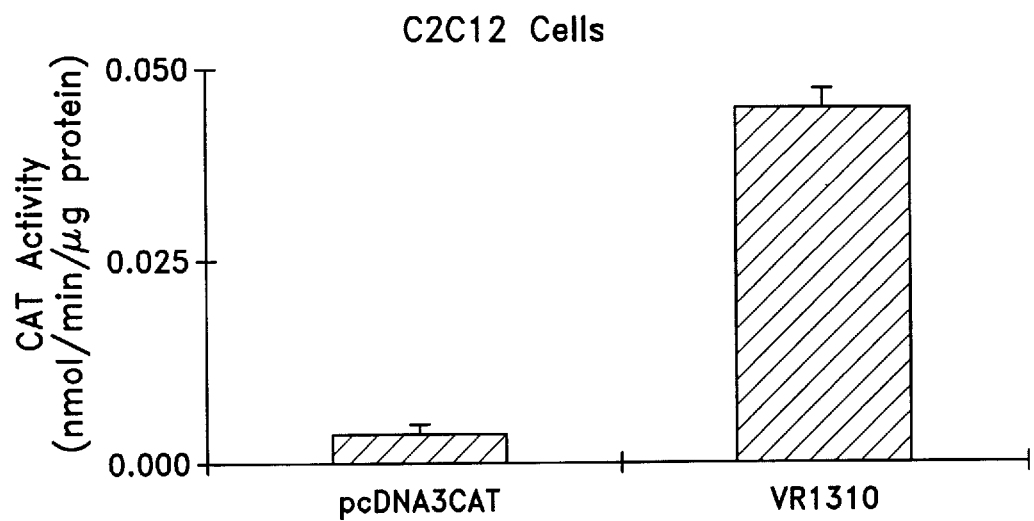
FIGS. 2A–2B. In vitro and in vivo comparison of hCMV-IE gene promoter/enhancer-based expression constructs. A, Cultured mouse myoblast C2C12 cells ($2\times10^5$) were transfected (in duplicate) with 2.5 $\mu$g of pcDNA3CAT or VR1310 using the lipid, DMRIE/DOPE (see Material and Methods). CAT assays were carried out 48 h after transfection. B, 5 $\mu$g (in 50 $\mu$l saline) of each plasmid DNA was injected into mouse rectus femoris muscle and the expression of CAT assayed 7 days post-injection (total n=20 muscles for each construct). Bars=standard error of the mean.
Figure 2B:
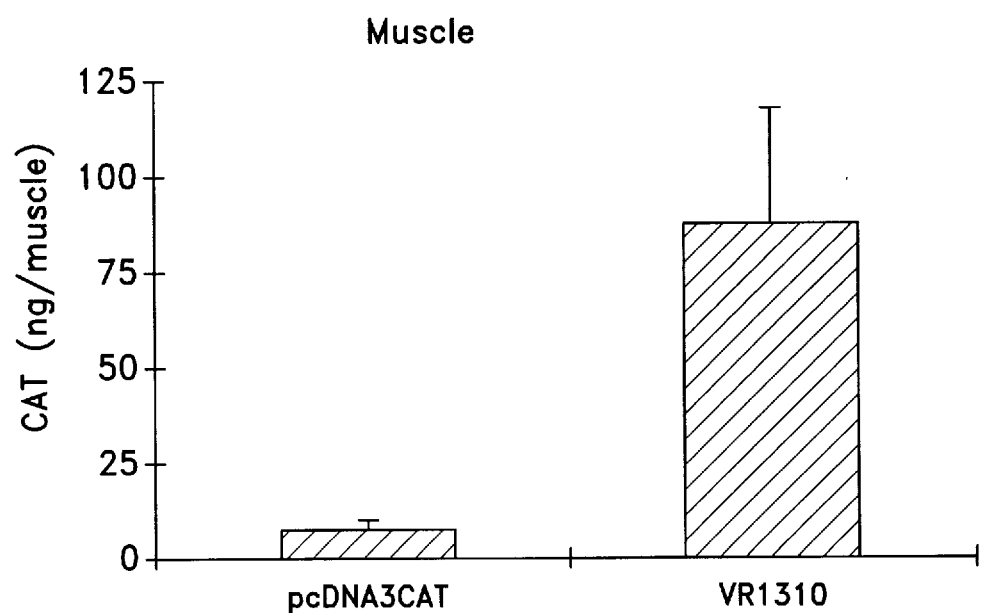

These vectors are initially tested in vitro to demonstrate a tetracycline-controlled activator system suitable for in vivo use. A hCMV-IE based CAT plasmid vector, designated VR1310 and shown in FIG. 1A, is developed following a systematic study of plasmid components required for high expression in transfected cells both in vitro and in vivo, and prepared as described above. Relative to the commercially available hCMV-IE expression plasmid pcDNA3-CAT, VR1310 expresses 10–20 fold more protein in transiently transfected C2C12 mouse myoblast cells in vitro (FIG. 2A) and 10 fold more protein upon injection into muscle tissue (FIG. 2B).

To determine the relative efficacy of using the chimeric tetracycline-controlled activator system (Gossen, M. & Bujard, H. *Proc Natl Acad Sci USA* 89, 5547–5551 (1992)), VR1310 expression is compared to expression obtained with the two plasmid system using pUHD15-1, a tetracycline-controlled activator expression plasmid, and pUHD3-1 CAT, a tetracycline-controlled activator dependent CAT expression plasmid. C2C12 cells co-transfected with these two plasmids express CAT protein at a level comparable to VR1310 (data not shown).

To test whether VR1310 expression might be further improved by making CAT transcription dependent upon the tetracycline-controlled activator, the hCMV-IE promoter/enhancer (−54 to −654 bp) is removed from VR1310 and replaced with seven repeats of the tetracycline operator sequence from pUHD3-1CAT, leaving the −53 to +1 hCMV-IE gene TATA box (and the 944 base hCMV-IE gene 5-prime untranslated region/intron A) downstream of the tetracycline operator sequences. This minimal promoter-containing plasmid is designated VR1312 (FIG. 1B) and its expression in transfected C2C12 cells is shown in FIG. 3.

Relative to VR1310, VR1312 transfected cells express very low levels of CAT protein. However, in cells co-transfected with pUHD15-1 and VR1312, CAT expression is induced more than 100 fold over VR1312 alone, reaching a level of expression that is approximately 4 fold greater than the parental VR1310. In addition, C2C12 cells co-transfected with VR1312 and pUHD15-1 and treated with tetracycline express less than 1% of the CAT activity seen in untreated cells. The results indicate that, in addition to its capacity to express high levels of CAT, VR1312 based CAT activity is completely dependent upon the co-expression of the tetracycline-controlled activator and that high expression can be repressed by tetracycline.

Figure 1B:
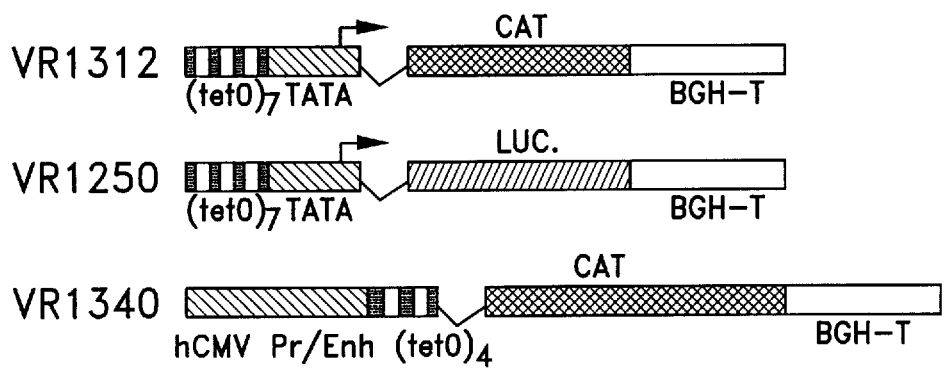
Figure 1C:
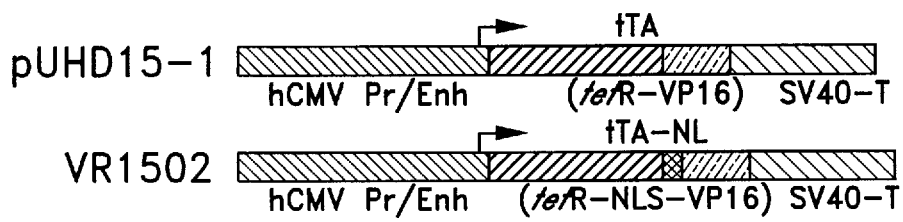

To further increase the tetracycline-controlled activator dependent CAT activity, the structure of the tetracycline-controlled activator fusion protein is modified to assist in post-translational targeting this largely prokaryotic protein to the eukaryotic nucleus. To do this, an oligonucleotide sequence encoding an in-frame basic nuclear localization signal peptide is inserted into the pUHD5-1 plasmid between the region encoding the tetracycline repressor and the VP16 activation domain in the tetracycline-controlled activator. Jans, D. & Jans, P. *Oncogene* 9,2961–2968 (1994); Deuschle, U., Meyer, & W., Thiesen, H-J. *Mol Cell Biol* 15, 1907–1914 (1995). This new plasmid, designated VR1502, expresses a nuclear localized tetracycline-controlled activator (FIG. 1C).

Figure 3:
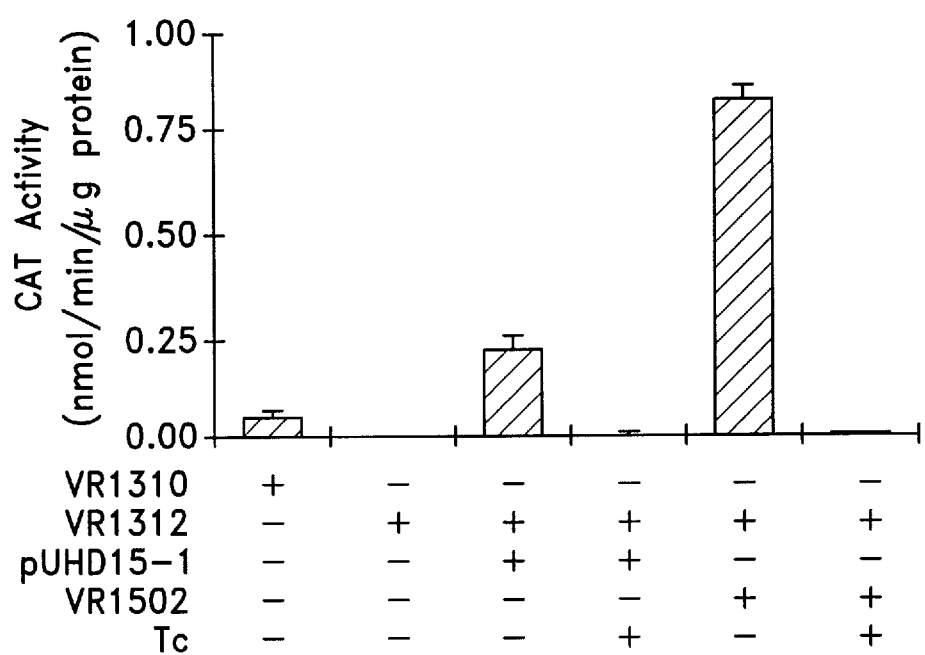
FIG. 3. Comparison of hCMV-IE gene promoter/enhancer-based and tTA-dependent expression vectors in vitro. Cultured mouse myoblast C2C12 cells ($2\times10^5$) were transfected with 2.5 µg of each plasmid DNA according to the key under the histogram. All transfections were done using the same total mass of DNA (10 µg), adding pUC19 plasmid DNA where necessary. In experiments using tetracycline (Tc), cells were pretreated with 1 µg/ml Tc for 24 hours prior to transfection and maintained in 1 µg/ml Tc until harvesting. CAT activity was assayed in cell lysates at 48 h post-transfection.

CAT assays of cells co-transfected with VR1312 and VR1502 indicate that VR1312 based CAT expression is nearly 4-fold greater than in co-transfections of cells using VR1312 with the original tetracycline-controlled activator expression plasmid, pUHD15-1 (FIG. 3). However, this 4-fold increase in expression remains completely dependent upon the nuclear localized tetracycline-controlled activator, such that when transfected cells are treated with tetracycline, the expression of CAT is virtually shut off (FIG. 3). Since VR1502 elicits significant enhancement of CAT expression, this nuclear localized tetracycline-controlled activator expression plasmid is used in all subsequent experiments.

In Vivo Testing

Figure 4:
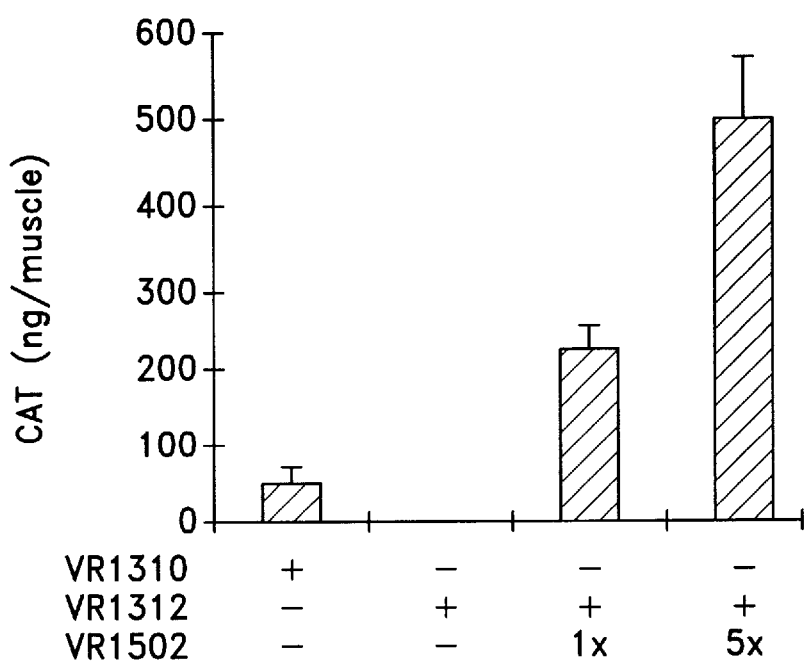
FIG. 4. Comparison of hCMV-IE gene promoter/enhancer-based and tTA-dependent expression vectors in vivo. 5 µg (in 50 µl saline) of reporter plasmids VR1310 or VR1312 were injected into mouse rectus femoris muscle and the expression of CAT assayed 7 days post-injection. For tTA-dependent expression, an equal amount (5 µg) or a 5 fold excess (25 µg) of plasmid VR1502 was co-injected with VR1312 (total n=20 muscles for each experiment) Error bar=standard error of the mean.

These vectors are next tested in vivo to demonstrate in vivo use of the tetracycline-controlled activator system. To compare nuclear localized tetracycline-controlled activator dependent VR1312 CAT expression in vivo with that of VR1310, five $\mu$g of VR1310, VR1312, or VR1312 with varying amounts of VR1502, are injected into the mouse rectus femoris muscle. The results are shown in FIG. 4. CAT expression is barely detectable (<200 pg/muscle) in muscle at seven days following injection of the VR1312 vector alone. However, co-injection of equimolar amounts of VR1502 with VR1312 results in more than a 1000 fold increase in expression (>200 ng/muscle), an expression level 2–3 fold higher than VR1310. Increasing the molar ratio of VR1502/VR1312 to 5 results in a further increase in CAT expression compared with that seen at the 1:1 ratio (FIG. 4).

Figure 5C:
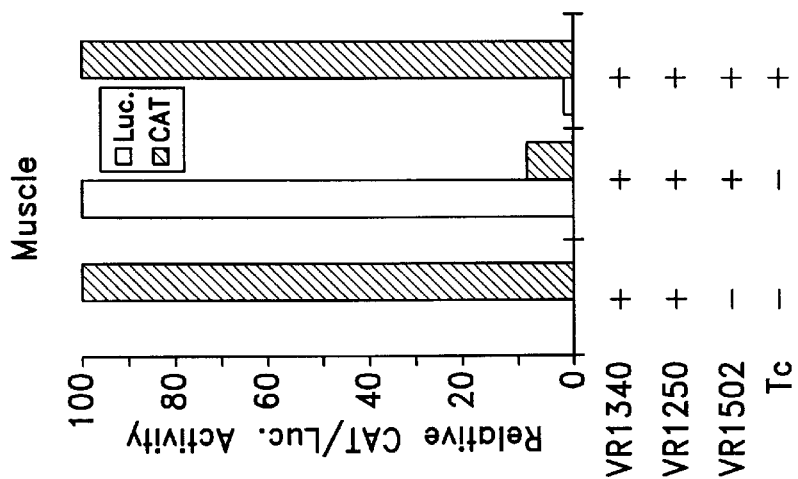
FIGS. 5A–5C. Alternate regulation of gene expression by tetracycline. A, up-regulation of CAT expression by tetracycline in vitro. Mouse myoblast C2C12 cells (105) were transfected with 2.5 µg of VR1310, 2.5 µg of VR1340, or 2.5 µg of VR1340 plus 2.5 µg of VR1502±1 µg/ml tetracycline (Tc). B, concurrent repression and induction of two genes by Tc in vitro and in vivo. $2\times10^5$ C2C12 cells were cotransfected with 1 µg each of VR1250 and VR1340 alone or 1 µg each of VR1250 and VR1340 along with 3 µg VR1502, ±1 µg/ml tetracycline. Mouse rectus femoris muscles were co-injected with 5 µg each of VR1250 and VR1340 or 5 µg of VR1250, VR1340 plus VR1502 with or without subcutaneous implants of Tc controlled release pellets. Luciferase and CAT were assayed 7 days post-injection (n=20 muscles for each experiment). Error bar=standard error of the mean. Carrier DNA (pUC19) was used when necessary to keep the total amount of DNA constant in the co-transfections or coinjections. Results were normalized to the highest values for each reporter=100% relative activity. The variations for the assays were less that 5% for in vitro experiments and less that 20% in vivo.
Figure 5B:
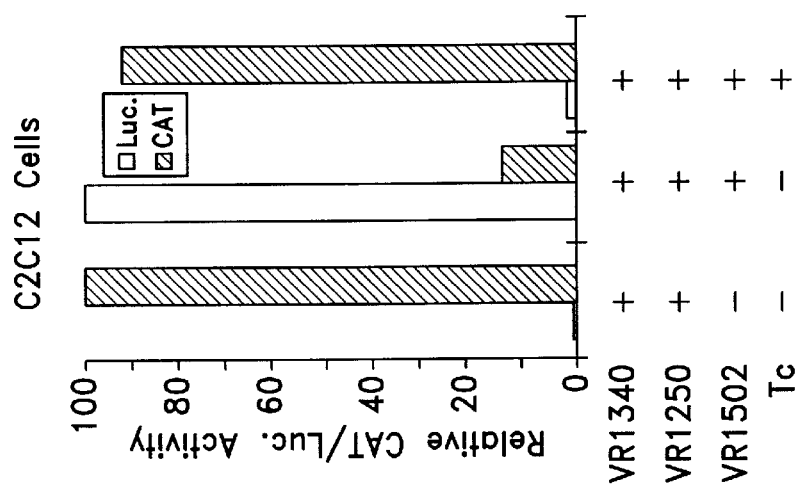
Figure 5A:
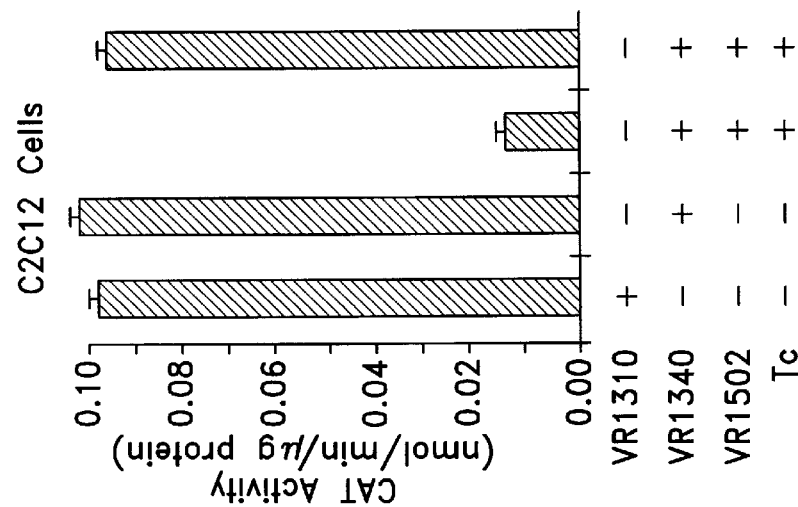

For gene therapy and gene immunization applications, it would be useful to activate as well as repress gene expression using an effector molecule, such as tetracycline. Tetracycline has been shown to transiently activate a tetracycline operator modified gene sequence in transgenic plant cells when gene transcription was repressed in cells co-expressing the tetracycline repressor protein. Gatz, C., Frohberg, C. & Wendenburg, R. *Plant J* 2, 397–404 (1992). To test this means of tetracycline activation in animal cells, VR1310 is modified by inserting 4 synthetic copies of the tetracycline operator sequence immediately downstream from the hCMV-IE promoter/enhancer (and 5-prime of the hCMV-IE untranslated region and intron A). The chimeric hCMV-IE promoter in this plasmid, designated VR1340 (FIG. 1B), is initially tested in vitro and the results are shown in FIG. 5A. The VR1340 plasmid expresses approximately the same level of CAT in transfected cells in vitro relative to the parental VR1310. This indicates that the addition of tetracycline operator sequences downstream from the promoter in VR1340 has no effect on CAT reporter expression in transfected cells. However, co-transfection of cells with VR1340 plus VR1502 decreases VR1340 based CAT activity nearly 10 fold, from 0.10 to approximately 0.01 nmol acetylated chloramphenicol/min/$\mu$g protein. Moreover, treatment of VR1340 and VR1502 co-transfected cells with tetracycline results in the restoration of VR1340 based CAT expression.

The inquiry arises whether two different genes can be alternatively regulated by tetracycline if cells are transfected using a combination of the plasmid vector constructs described above. In answer, a nuclear localized tetracycline-controlled activator dependent firefly luciferase expression vector (VR1250) is made so as to be structurally analogous to VR1312 (FIG. 1B). To initially test these new constructs in cells in vitro, mouse C2C12 cells are co-transfected with plasmids VR1340 and VR1250 in the presence or absence of VR1502, with and without tetracycline. The results are shown in FIG. 5B. In the absence of the nuclear localized tetracycline-controlled activator expression plasmid (i.e., VR1502), cells co-transfected with VR1340 and VR1250 show high levels of CAT expression and very low levels of luciferase expression. The relative expression of these two reporter proteins is reversed in cells co-transfected with VR1502, where a 5 fold increase in VR1340 based CAT expression is observed and more than a 100 fold increase in VR1250 based luciferase expression. The relative expression of these two reporter proteins is again reversed in cells transfected in the presence of tetracycline. In such tetracycline co-transfected cells, VR1250 luciferase expression is reduced to very low levels and VR1340 based CAT expression is restored to the level seen without VR1502.

To evaluate the possibility of differential regulation of reporter gene expression in vivo, these same plasmid combinations are injected into mouse skeletal muscle. The results are shown in FIG. 5B. In the absence of VR1502, VR1250 based luciferase expression is virtually undetected in muscle and VR1340 based CAT expression is high, comparable to the levels of expression seen using VR1310. Muscles injected with nearly equal molar amounts of VR1340, VR1250, and VR1502 reverse this activity profile; VR1340 based CAT expression is repressed 10 fold by the presence of nuclear localized tetracycline-controlled activator in muscle cells while, at the same time, luciferase expression is induced by more than 1000 fold. Injection of these three plasmids into animals receiving tetracycline exhibit reporter expression at levels similar to those seen without the nuclear localized tetracycline-controlled activator expressing VR1502 plasmid. These results indicate the ability of the nuclear localized tetracycline-controlled activator to simultaneously activate and repress the transcriptional activity of plasmid DNA in vivo.

Bicistronic Expression Vector

Figure 1D:
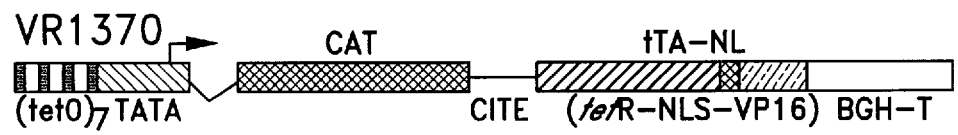
Figure 6:
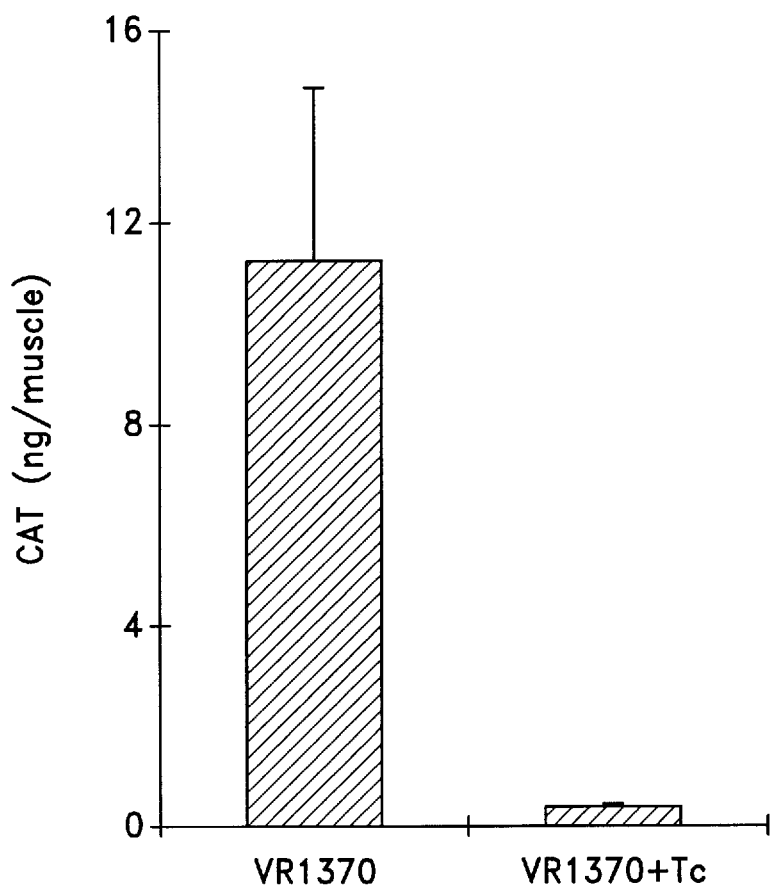
FIG. 6. Tetracycline-regulated CAT expression in vivo using a bicistronic plasmid construct. 5 µg of plasmid VR1370 were injected into mouse rectus femoris muscles as described above in the presence and absence of subcutaneously administered Tc. CAT assays were performed 7 days post-injection. (Total n=20 muscles for each experiment). Error bar=standard error of the mean.

Ultimately, a single plasmid DNA, designated VR1370, is constructed as a tetracycline-controlled activator bicistronic expression vector. VR1370, as shown in FIG. 1D, is a nuclear localized tetracycline-controlled activator dependent expression vector having a CAT coding sequence positioned downstream of the seven repeated tetracycline operator sequences, the −53 to +1 hCMV-IE gene TATA box (i.e., the minimal promoter), and the 944 base hCMV-IE gene 5-prime untranslated region and intron A sequence. Thus, the nuclear localized tetracycline-controlled activator dependent control region is the same as in VR1312 (compare FIG. 1B and FIG. 1D). The CAT coding sequence is followed immediately by the encephalomyocarditis virus CAP Independent Translational Enhancer (CITE) sequence, an internal translational control element able to effect independent translation of the downstream nuclear localized tetracycline-controlled activator coding sequence on this bicistronic mRNA. Elroy-Stein, O., Fuerst, T., Moss, B., *Proc Natl Acad Sci USA* 86, 6126–6130 (1989); Morgan, T., et al. *Nucl Acids Res* 20, 1293–9 (1992). By coupling nuclear localized tetracycline-controlled activator expression to CAT expression using a bicistronic mRNA, VR1370 is designed to incorporate both the tetracycline-controlled activator and the reporter protein sequence into a single, self-accelerating and tetracycline regulated plasmid vector. To test VR1370 expression in vivo, plasmid DNA is injected into mouse muscle tissue and CAT expression is measured at seven days. As shown in FIG. 6, VR1370 expresses CAT at a comparatively low level when measured at seven day post-injection time point. The level is approximately 40 fold less than that seen in muscle tissue co-injected with VR1312 and VR1502. However, when VR1370 is injected into animals receiving systemic tetracycline, the level of CAT expressed in muscle is reduced to less than 2.5% of that seen in animals not receiving tetracycline. Such a result indicates that expression of CAT using the single plasmid construct can be more tightly regulated with tetracycline relative to that achieved using the two plasmid vectors, as shown in FIG. 5.

VR1370 has been deposited. The name and address of the depository is American Type Culture Collection (ATCC), Rockville, Md., U.S.A. The accession number for the deposit is ATCC 97467. The date of the deposit is Mar. 7, 1996.

Gene Therapy and Gene Immunization

These results demonstrate that a high expression plasmid, designed for transfecting cells in vitro and in vivo, can be constructed to make expression wholly dependent upon a tetracycline regulated chimeric activator. This new plasmid, when co-transfected with a second plasmid encoding the activator, effects higher levels of expression than the parental vector with its human cytomegalovirus immediate early gene (hCMV-IE) enhancer/promoter. This high level of expression is dependent upon binding of the transacting protein to cis control elements, i.e., tetracycline operator sequence(s), and binding is regulated by the common antibiotic, tetracycline. Additionally, by adjusting the position of the tetracycline operator sequence(s), the expression of a reporter gene can also be either activated or repressed by the transacting protein. Furthermore, it is shown that a single plasmid construct, designed to express a bicistronic mRNA encoding both the transcription factor and a reporter protein, can also be used to effect significant levels of effector-regulated expression. Levels may go even higher after 7 days (the timepoint measured), when the single vector construct has enough time for maximal attainment of full activator expression and subsequent full expression of reporter protein. Such results indicate that coding sequences carried by these plasmid DNAs can be regulated to deliver desired levels of proteins in vivo for the purpose of gene therapy and gene immunization.

Accordingly, FIG. 1D illustrates one embodiment of the invention in which a eukaryotic expression vector is provided as a single plasmid able to turn off a clinically beneficial protein of interest using the molecule, tetracycline, when the CAT encoding sequence is replaced by the sequence encoding the protein of interest. This construct places a transcription unit under the control of a tetracycline-controlled activator-responsive promoter. The promoter features a tetracycline operator sequence upstream of a minimal promoter. The transcription unit includes two cistrons, one encoding the tetracycline-controlled activator, which comprises a tetracycline repressor protein fused to a transcription activation domain, and the other encoding the protein of interest. These cistrons are separated by an internal ribosome entry site, such as the CITE sequence, to permit translation of the bicistronic message in eukaryotic cells.

In operation, the tetracycline-controlled activator is produced, because of leaky gene expression. This gene regulatory protein activates transcription of the bi-cistronic message by binding the tetracycline-controlled activator-responsive promoter. Such binding results in production of the protein of interest and more and more activator. The expression of the tetracycline-controlled activator is accordingly amplified by this control mechanism. Then, by the addition of tetracycline, the DNA binding activity of the tetracycline-controlled activator is suppressed by bound tetracycline so it can no longer activate expression of the protein of interest nor contribute any longer to amplification of its own production. Gene transcription of the protein of interest is thereby repressed.

Figure 7:
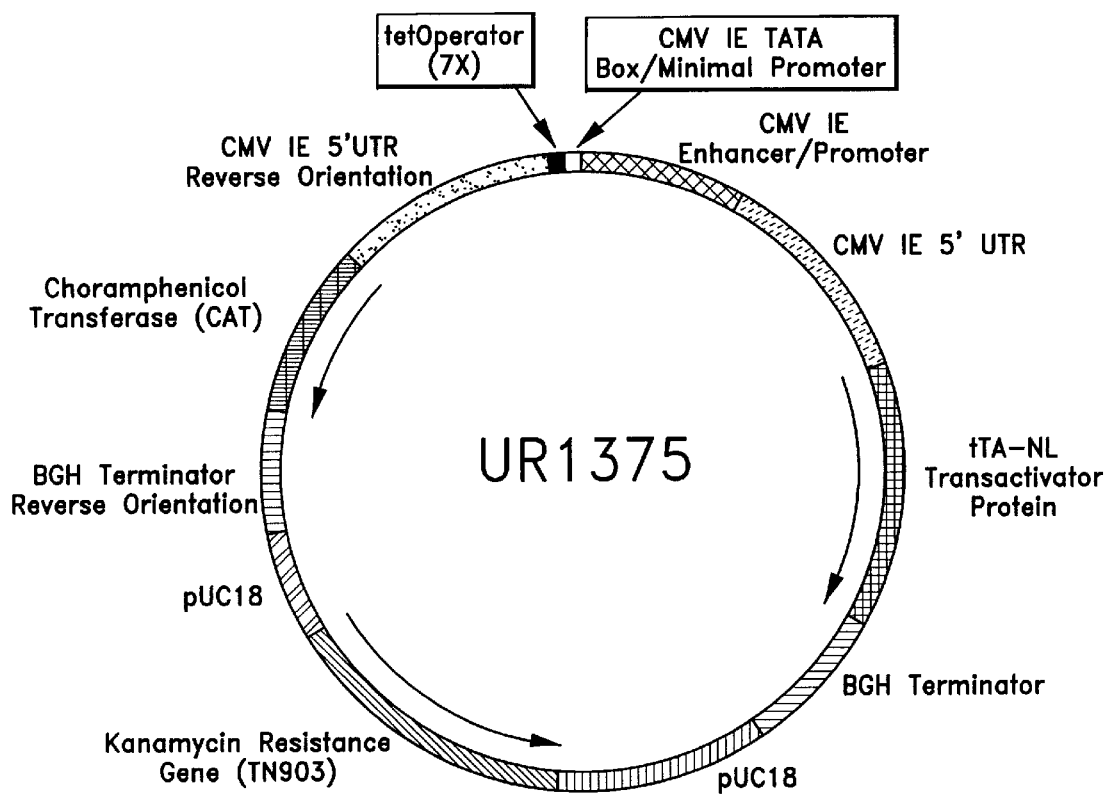
FIG. 7. Tetracycline-regulated CAT expression vector having a bidirectional CMV enhancer/promoter control element. This construct places two transcription units in reverse orientation, with an enhancer being a shared element.
Figure 7:
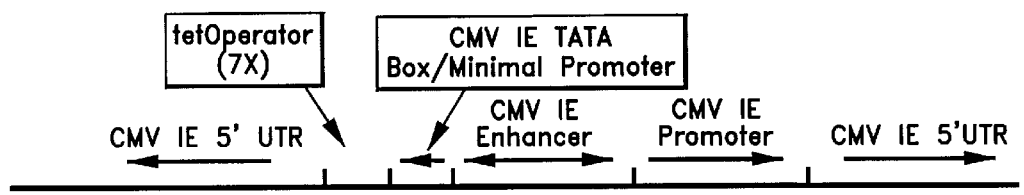

FIG. 7 illustrates another embodiment of the invention in which a eukaryotic expression vector is provided as a single plasmid able to turn on a clinically beneficial protein of interest using tetracycline. This construct places two transcription units in reverse orientation, with an enhancer being a shared element. The first transcription unit includes a tetracycline-controlled activator-responsive promoter linked to the sequence encoding the protein of interest. This promoter positions a tetracycline operator sequence downstream of a eukaryotic enhancer and promoter to control expression of the protein of interest. The second transcription unit encompasses a eukaryotic enhancer and promoter linked to the sequence encoding a tetracycline-controlled activator, which comprises a tetracycline repressor protein fused to a transcription activation domain. Here, the eukaryotic promoter and enhancer, the enhancer being common to both transcription units, are oriented in opposite directions.

In operation, the tetracycline-controlled activator is produced because the CMV IE gene enhancer/promoter is a constitutive promoter. This gene regulatory protein represses the transcription of the message encoding the protein of interest by binding the tetracycline-controlled activator-responsive promoter. Such binding operates, by virtue of the tetracycline operator sequence being positioned downstream of the CMV IE gene enhancer/promoter, to repress production of the protein of interest. The expression of the tetracycline-controlled activator is not affected by this control mechanism. Then, in the presence of tetracycline, the DNA binding activity of the tetracycline-controlled activator is suppressed by bound tetracycline so it can no longer repress expression of the protein of interest. Gene transcription of the desired protein is thereby activated.

The invention also provides these vectors in combination, so that tetracycline is used to turn on the expression of one gene and simultaneously turn off the expression of another gene. These vectors can be delivered to the same cells, or to different cells, for example, in another body tissue. Tetracycline can then function to activate expression of one protein and repress expression of another protein, for example, to maximize responses by increasing one enzyme catalyzing a reaction and at the same time decreasing another enzyme that catalyses the opposite reaction. These vectors therefore have utility in gene therapy and gene immunization, both singly and in combination.

A large number of diseases can benefit from administration of molecules, i.e., peptides, polypeptides, and proteins, that induce a desired therapeutic effect in a host vertebrate. These include lymphokines, e.g., interleukin-2, tumor necrosis factor, and the interferons; growth factors, e.g., nerve growth factor, epidermal growth factor, and human growth hormone; LDL receptor; tissue plasminogen activator; blood coagulating factors, e.g., Factor VIII, Factor IX; granulocyte-macrophage colony-stimulating factor; erythropoietin; insulin; calcitonin; thymidine kinase; dystrophin; CFTR; and the like. They also include toxins (e.g., ricin, diphtheria toxin, and cobra venom factor) which are delivered to diseased or neoplastic cells, where they can have major therapeutic benefits. They further include antibodies, anti-idiotypic antibodies, MHC molecules, and fragments and chimeras thereof.

Many diseases are amenable to vaccination with immunogens that stimulate a protective immune response in a host vertebrate, for example, infectious diseases caused by viruses, parasites, bacteria, etc. Such immunogens include cancer associated antigens, for vaccination against cancer, and antigens that vaccinate against AIDS. These immunogens also include antigens that are presented as peptides within MHC molecules, and the like.

The invention accordingly provides agents suitable for use in gene therapy and gene immunization, i.e., as drugs and vaccines. These drugs comprise the eukaryotic expression vectors described here, preferably single construct vectors, in a physiologically-acceptable carrier where the gene product is a molecule that induces a desired therapeutic effect in a host vertebrate. The vaccines comprise these eukaryotic expression vectors, in a physiologically-acceptable carrier, where the gene product is an immunogen that stimulates a protective immune response in a host vertebrate.

These vectors may be delivered to body tissues of host vertebrates, preferably to the interstitial space thereof. These body tissues include muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Delivery to muscle tissue is preferred, especially skeletal muscle tissue.

The gene regulatory proteins of this invention, especially those of non-human origin, may require that the patient be immunosuppressed to preclude rejection. While an activation system may only require the production of a few gene regulatory proteins to turn on expression, in contrast to a repression system where a large number of gene regulatory proteins is considered necessary to sufficiently keep expression turned off, immunosuppression may nevertheless be required in either system. Immunosuppression reagents are contemplated for this purpose, for example, cyclosporin. Treatment with immunosuppression reagents is well within the level of skill in the relevant art.

Vectors for injection, a preferred route of delivery, may be prepared in unit dosage form in ampules, or in multidose containers. The vectors may be present in such forms as suspensions, solutions, or emulsions in oily or preferably aqueous vehicles. Alternatively, the vector may be in lyophilized form for reconstitution, at the time of delivery, with a suitable vehicle, such as sterile pyrogen-free water (optionally, for subsequent combination with a lipid or other facilitator of transfection). Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of body tissues is preferred, although other parenteral routes, such as inhalation of an aerosol formulation, may be required in specific administration, as for example to the mucous membranes of the nose, throat, bronchial tissues or lungs.

In preferred protocols, a formulation comprising the vector in an aqueous carrier is injected into tissue in amounts of from 10 $\mu$l per site to about 1 ml per site. The concentration of vector in the formulation is from about 0.1 $\mu$g/ml to about 20 mg/ml.

EXAMPLES

Particular aspects of the invention may be more readily understood by reference to the following examples, which

Example 1

Materials and Methods

Materials

[³H]-Acetyl CoA was purchased from DuPont New England Nuclear (Boston, Mass.). Luciferase substrate and lysis buffer were purchased from Promega (Madison, Wis.). The cationic lipid DMRIE (1,2-dimyristoyloxypropyl-3-dimethyl ammonium bromide) and the neutral lipid DOPE (dioleoyl phosphatidylethanolamine) used for in vitro transfection experiments were prepared as described. Felgner, J. H., et al. *J Biol Chem* 269, 2550–2561 (1994). All other chemicals were purchased from Sigma Chemical Corp (St. Louis, Mo.). DNA oligonucleotides used for cloning were synthesized by Genosys (Woodlands, Tex.). 4 to 12-week-old female BALB/c mice were purchased from Harlan Sprague-Dawley (San Diego, Calif.).

Plasmid Vectors

Plasmids pUHD10–3, containing the chimeric tetracycline operator sequence (tetO)/hCMV-IE TATA box, and pUHD15-1, expressing the tetracycline-controlled activator (tTA), were purchased from the Center for Molecular Biology, University of Heidelberg. Gossen, M. & Bujard, H. *Proc Natl Acad Sci USA* 89, 5547–5551 (1992). Expression vector pcDNA3 was purchased from Invitrogen (San Diego, Calif.). Vectors pUHD10-3CAT and pcDNA3CAT (FIG. 1) were constructed by inserting a SalI-BamHI fragment containing chloramphenicol acetyltransferase (CAT) from pBS-CAT (Promega) into SalI-BamHI-cut pUHD10-3 and pcNDA3, respectively. Plasmid VR1310 (FIG. 1) was constructed by inserting the same CAT fragment into a parental vector, VCL010, which is a modified derivative of p-CMVint-BL. Manthorpe, M., et al. *Hum Gene Ther* 4, 419–431 (1993). The modifications included removing the SV40 origin of replication, replacing the SV40 transcription terminator with the one from bovine growth hormone (BGH) gene, replacing the bacterial β-lactamase gene for ampicillin resistance with the gene encoding aminoglycoside 3'-phosphotransferase for kanamycin resistance from Tn903, and insertion of a multiple cloning site. Lew, D., et al. *Hum Gene Ther* 6, 553–564 (1995). This plasmid also contained the hCMV-IE gene 5-prime untranslated region and intron A sequence. Chapman, B. S., Thayer, R. M., Vincent, K. A. & Haigwood, N. L. *Nucl Acids Res* 19, 3979–3986 (1991); Choi, T., Huang, M., Gorman, C. & Jaenisch, R. *Mol Cell Biol* 11, 3070–3074 (1991). Vector VR1312 (FIG. 1) was made by replacing the hCMV-IE promoter/enhancer (a AvrII/Klenow to SacII fragment) in VR1310 with a XhoI/Klenow to SacII segment containing the chimeric tet operator sequence/hCMV-IE minimal promoter from pUHD10-3 (FIG. 1). Plasmid VR1250 (FIG. 1) was given the same backbone as VR1312 with the luciferase coding sequence replacing CAT. Manthorpe, M., et al. *Hum Gene Ther* 4, 419–431 (1993). VR1502 (FIG. 1) was made by inserting synthetic complementary DNA fragments (GTA CGG CAC CCA AGA AGA AGC GGA AGG TCC CAG GTG TAC CGA GCT CGA ATT GCG) (SEQ ID NO:1) encoding a nuclear localization signal (KKKRK) (SEQ ID NO:2) in frame between the (tetracycline repressor) tetR and VP16 domains (SpeI site) of the tTA protein encoded by pUHD15-1. Jans, D. & Jans, P. *Oncogene* 9, 2961–2968 (1994); Deuschle, U., Meyer, & W., Thiesen, H-J. *Mol Cell Biol* 15, 1907–1914 (1995). To construct VR1340 (FIG. 1), complementary oligonucleotide sequences representing 4 repeats of the tetracycline operator sequence were synthesized and inserted into a SacI site 4 bp downstream from the hCMV-IE promoter/enhancer, i.e., 3-prime of the TATA box, and 5-prime of the hCMV-IE untranslated region and intron A. Gatz, C., Frohberg, C. & Wendenburg, R. *Plant J* 2, 397–404 (1992). VR1370 was constructed by ligating three DNA fragments together. The first was a BamHI digested VR1312 vector DNA. This fragment provided a chimeric promoter containing 7 repeats of tetracycline operator sequences (7 repeats) and hCMV-IE gene minimal promoter plus intron A connected to a fragment encoding CAT. The second was the EcoR1 BamHI fragment from VR1502. This second fragment provided the coding sequence for the tetracycline repressor/NL/VP16 fusion protein. The third was a PCR'd fragment from a commercially available plasmid pCITE (Novagen, Inc., Madison, Wis.) using a 5-prime primer with a BglII restriction site and a 3-prime primer with a EcoRI restriction site. Ligation and cloning was performed by the usual protocols and could be carried out by those in the art. The clones recovered from this ligation could be restriction endonuclease digested to map and thus ensure correct orientation of the fragments within the final construct.

In vitro transfections

Duplicates of cultured C2C12 cells ($2 \times 10^5$) were transfected using 5 µg of plasmid DNA and lipids DMRIE/DOPE (50:50). The lipid/DNA ratio was 1. Feigner, J. H., et al. *J Biol Chem* 269, 2550–2561 (1994). Using these conditions, the expression of reporter protein in replicate samples was highly reproducible with a coefficient of variation of less than 10%. Feigner, J. H., et al. *J Biol Chem* 269, 2550–2561 (1994). To compare the activities of different expression constructs, the amount of plasmid DNA used in each transfection was kept constant by adding carrier plasmid DNA (pUC19).

Direct intramuscular DNA injection

Plasmid DNA used for in vivo studies was purified and evaluated for contaminants. Sambrook, J., Frisch, E. F. & Maniatis, T. T *Molecular Cloning: A Laboratory Manual* (Cold Spring Harbor Laboratory Press, Cold Spring Harbor, N.Y., 1989); Horn, N., Meek, J., Budahazi, G. & Marquet, M. *Hum Gene Ther* 6, 565–573 (1995). All plasmid preparations were greater than 50% supercoiled DNA and free of detectable protein and carbohydrates. Endotoxin levels were <60 EU/µg plasmid DNA. Direct DNA injection into rectus femoris muscle was performed as previously described. Manthorpe, M., et al. *Hum Gene Ther* 4, 419–431 (1993). Briefly, mice were injected with a 50 µl DNA/saline solution, at room temperature, using a 25G ½ inch needle which was collared to limit penetration to 2 mm in muscle tissue. In animal experiments involving systemic administration of tetracycline, a slow release pellet (0.7 mg/ml/day, Innovative Research of America, Toledo, Ohio) was implanted subcutaneous in the shoulder 24 to 48 h before DNA injection. All experimental protocols using animals were conducted under the guidelines provided by the American Association for Laboratory Animal Care.

Luciferase and CAT assays

The luciferase and CAT enzymes were assayed in extracts from either cultured cell lysates or in homogenized mouse muscle. For cultured cells, washed plates were scraped and the cells pelleted by centrifugation prior to resuspension in Reporter Lysis Buffer (Promega, Madison, Wis.). For injected muscle, the entire quadriceps muscle (150–200 mg, wet weight) was collected from euthanized (Euthanasia-5, 4.5 mg/muscle, i.p.) mice. The muscle tissue was quick frozen, and pulverized to a fine powder by grinding at −60° C. with 0.4 ml frozen volume of Reporter Lysis Buffer in a 1.5 ml conical centrifuge tube.

The frozen powder was subsequently thawed with 0.1 ml of lysis buffer, vortexed for 15' at room temperature, frozen and thawed 3× in liquid nitrogen and room temperature baths, and centrifuged for 3' at 10,000×g. The supernatant was removed and pooled with the second supernatant derived from a 0.5 ml lysis buffer volume used to re-extract the pellet (repeat of the extraction procedure above, without the freeze/thaw step). Luciferase activity was assayed according to published methods. The luciferase standard curve was linear from 1 to 100,000 pg of protein (luciferase specific activity: $1.0-2.0 \times 10^{13}$ RLU/mg protein; Analytical Luminescence Labs). CAT activity was assayed using a two-phase extraction method as previously described. Sankaran, L. *Anal Biochem* 200, 180–186 (1992). Cell and tissue samples were initially treated at 60° C. for 10 min followed by incubation with CAT substrates at 37° C for 2 to 3 h. A standard curve was made using muscle extract and known amounts of commercial CAT enzyme (Sigma Chemicals Corp., St. Louis, Mo.; S.A.: 106,400 units/mg protein). Under the above conditions, the linear range of the assay was from I to 1000 pg of the CAT protein.

Results tTA-dependent Activation System

A hCMV-IE based CAT plasmid vector, designated VR1310 and shown in FIG. 1A, was developed following a systematic study of plasmid components required for high expression in transfected cells both in vitro and in vivo. Relative to the commercially available hCMV-IE expression plasmid pcDNA3-CAT, VR1310 expressed 10–20 fold more protein in transiently transfected C2C12 mouse myoblast cells in vitro (FIG. 2A) and 10 fold more protein upon injection into muscle tissue (FIG. 2B).

To determine the relative efficacy of using the chimeric tetracycline-controlled activator (tTA) system (Gossen, M. & Bujard, H. *Proc Natl Acad Sci USA* 89, 5547–5551 (1992)), VR1310 expression was compared to expression obtained with the two plasmid system using pUHD15-1, a tTA expression plasmid, and pUHD3-1 CAT, a tTA dependent CAT expression plasmid. C2C12 cells co-transfected with these two plasmids expressed CAT protein at a level comparable to VR1310 (data not shown).

To test whether VR1310 expression might be further improved by making CAT transcription dependent upon the heterologous activator, tTA, the hCMV-IE promoter/enhancer (−54 to −654 bp) was removed from VR1310 and replaced with seven repeats of the tetracycline operator sequence (tetO$_7$) from pUHD3-1 CAT. This manipulation left the −53 to +1 hCMV-IE gene TATA box (and the 944 base hCMV-IE gene 5-prime untranslated region/intron A) downstream of the control element. This minimal promoter-containing plasmid was designated VR1312 (FIG. 1B) and its expression in transfected C2C12 cells is shown in FIG. 3.

Relative to VR1310, VR1312 transfected cells expressed very low levels of CAT protein. However, in cells co-transfected with pUHD15-1 and VR1312, CAT expression was induced more than 100 fold over VR1312 alone, reaching a level of expression that was approximately 4 fold greater than the parental VR1310. In addition, C2C12 cells co-transfected with VR1312 and pUHD15-1 and treated with 1 µg/ml tetracycline (Tc) during the 48 hour transient transfection period expressed less than 1% of the CAT activity seen in untreated cells. The results indicate that, in addition to its capacity to express high levels of CAT, VR1312 based CAT activity is completely dependent upon the co-expression of the tTA transacting protein and that high expression can be repressed by tetracycline.

To further increase the tTA-dependent CAT activity, the structure of the tTA fusion protein was modified to assist in post-translational targeting this largely prokaryotic protein to the eukaryotic nucleus. To do this, an oligonucleotide sequence encoding an in-frame basic nuclear localization signal peptide was inserted into the pUHD5-1 plasmid between the coding region of the tetracycline receptor (tetR) and the VP16 activation domain in tTA. Jans, D. & Jans, P. *Oncogene* 9, 2961–2968 (1994); Deuschle, U., Meyer, & W., Thiesen, H-J. *Mol Cell Biol* 15, 1907–1914 (1995). This new plasmid, designated VR1502, expressed a nuclear localized tTA protein termed tTA-NL (FIG. 1C).

CAT assays of cells co-transfected with VR1312 and VR1502 indicated that VR1312 based CAT expression was nearly 4-fold greater than in co-transfections of cells using VR1312 with the original tTA expression plasmid, pUHD15-1 (FIG. 3). However, this 4-fold increase in expression remained completely dependent upon the transcription factor, tTA-NL, such that when transfected cells were pre-treated with 1 µg/ml Tc, the expression of CAT was virtually shut off (FIG. 3). Since VR1502 elicited significant enhancement of CAT expression, this tTA-NL expression plasmid was used in all subsequent experiments.

tTA-NL dependent CAT Expression in vivo

To compare tTA-NL dependent VR1312 CAT expression in vivo with that of VR1310, five µg of VR1310, VR1312, or VR1312 with varying amounts of VR1502, were injected into the mouse rectus femoris muscle, as described in Materials and Methods. The results are shown in FIG. 4. CAT expression was barely detectable (<200 pg/muscle) in muscle at seven days following injection of the VR1312 vector alone. However, co-injection of equimolar amounts of VR1502 with VR1312 resulted in more than a 1000 fold increase in expression (>200 ng/muscle), an expression level 2–3 fold higher than VR1310. Increasing the molar ratio of VR1502NR1312 to 5 resulted in a further increase in CAT expression compared with that seen at the 1:1 ratio (FIG. 4).

Tetracycline Induced Gene Expression

For gene therapy and gene immunization applications, it would be useful to activate as well as repress gene expression using a small, clinically acceptable, effector molecule such as Tc. Tc was shown to transiently activate a tetO modified gene sequence in transgenic plant cells when gene transcription was repressed in cells co-expressing tetR protein. Gatz, C., Frohberg, C. & Wendenburg, R. *Plant J* 2, 397–404 (1992). To test this means of Tc activation in animal cells, VR1310 was modified by inserting 4 synthetic copies of the tetO sequence (tetO$_4$) immediately downstream from the hCMV-IE promoter/enhancer, that is, 3-prime of the TATA box, and 5-prime of the hCMV-IE untranslated region and intron A. The chimeric hCMV-IE promoter in this plasmid, designated VR1340 (FIG. 1B), was initially tested in vitro and the results are shown in FIG. 5A. The VR1340 plasmid expressed approximately the same level of CAT in transfected cells in vitro relative to the parental VR1310. This indicates that the addition of tetO$_4$ sequences downstream from the TATA box in VR1340 had no effect on CAT reporter expression in transfected cells. However, co-transfection of cells with VR1340 plus VR1502 decreased VR1340 based CAT activity nearly 10 fold, from 0.10 to approximately 0.01 nmol acetylated chloramphenicol/min/µg protein. Moreover, treatment of VR1340 and VR1502 co-transfected cells with Tc resulted in the restoration of VR1340 based CAT expression.

These results prompted the inquiry whether two different genes could be alternatively regulated by tetracycline if cells were transfected using a combination of the plasmid vector constructs described above. To demonstrate this, a tTA-NL dependent firefly luciferase expression vector (VR1250) was made so as to be structurally analogous to VR1312 (FIG. 1B). To initially test these new constructs in cells in vitro, mouse C2C12 cells were co-transfected with plasmids VR1340 and VR1250 in the presence or absence of VR1502, with and without tetracycline. The results are shown in FIG. 5B. In the absence of the tTA-NL expression plasmid (i.e., VR1502), cells co-transfected with VR1340 and VR1250 showed high levels of CAT expression and practically no luciferase expression. The relative expression of these two reporter proteins was reversed in cells co-transfected with VR1502. The relative expression of these two reporter proteins was again reversed in cells transfected in the presence of 1 μg/ml Tc. In such Tc co-transfected cells, VR1250 luciferase expression was reduced to very low levels and VR1340-based CAT expression was restored to the level seen without VR1502.

To evaluate the possibility of differential regulation of reporter gene expression in vivo, these same plasmid combinations were injected into mouse skeletal muscle. The results are shown in FIG. 5B. In the absence of VR1502, VR1250 based luciferase expression was virtually undetected in muscle and VR1340 based CAT expression was high, comparable to the levels of expression seen using VR1310. Muscles injected with nearly equal molar amounts of VR1340, VR1250, and VR1502 reversed this activity profile; VR1 340 based CAT expression was repressed 10 fold by the presence of tTA-NL in muscle cells while, at the same time, luciferase expression was induced by more than 1000 fold. Injection of these three plasmids into animals receiving tetracycline exhibited reporter expression at levels similar to those seen without the tTA-NL expressing VR1502 plasmid. These results indicate the ability of the chimeric tTA-NL transacting protein to simultaneously activate and repress the transcriptional activity of plasmid DNA in vivo using the Tc-regulated activator.

A tTA Regulated Bicistronic Expression Vector

The experiments presented above require cell transfections with 2 or more plasmid DNAs that must enter each transfected cell nucleus in order to manifest the necessary regulatory effect. To remedy this, a single plasmid DNA, designated VR1370, was constructed. VR1370, as shown in FIG. 1D, was a tTA-NL dependent expression vector having a CAT coding sequence positioned downstream of the tetO$_7$ response elements, the -53 to +1 hCMV-IE gene TATA box (i.e., the minimal promoter), and the 944 base hCMV-IE gene 5-prime untranslated region and intron A sequence. Thus, the tTA-NL dependent control region was the same as in VR1312 (compare FIG. 1B and FIG. 1D). The CAT coding sequence was followed immediately by the encephalomyocarditis virus CAP Independent Translational Enhancer (CITE) sequence, an internal translational control element able to effect independent translation of the downstream tTA-NL coding sequence on this bicistronic mRNA. Elroy-Stein, O., Fuerst, T., Moss, B., *Proc Natl Acad Sci USA* 86, 6126–6130 (1989); Morgan, T., et al. *Nucl Acids Res* 20, 1293–9 (1992). By coupling tTA-NL protein expression to CAT expression using a bicistronic mRNA, VR1370 was designed to incorporate both the tTA-NL and the reporter protein sequence into a single, self-accelerating and Tc controlled plasmid vector. To test VR1370 expression in vivo, plasmid DNA was injected into mouse muscle tissue and CAT expression was measured at seven days. As shown in FIG. 6, VR1370 expressed CAT at a comparatively low level when measured at seven day post-injection time point. The level was approximately 40 fold less than that seen in muscle tissue co-injected with VR1312 and VR1502. However, when VR1370 was injected into animals receiving systemic Tc, the level of CAT expressed in muscle was reduced to less than 2.5% of that seen in animals not receiving Tc. Such a result indicates that expression of CAT using the single plasmid construct can be more tightly regulated with Tc relative to that achieved using the two plasmid vectors, as shown in FIG. 5.

While the invention has necessarily been described in conjunction with preferred embodiments and specific working examples, one of ordinary skill in the art, after reading the foregoing specification, will be able to effect various changes, substitutions of equivalents, and alterations to the subject matter, without departing from the spirit and scope of the invention. Hence, the invention can be practiced in ways other than those specifically described here. It is therefore intended that any protection granted be limited only by the appended claims and their equivalents.

What is claimed is:

1. A self-accelerating eukaryotic expression vector comprising a single transcription unit under the control of a tetracycline-controlled activator-responsive promoter, said unit comprising a first cistron encoding a desired gene product and a second cistron encoding said tetracycline-controlled activator, and an internal ribosome entry site positioned between said cistrons.

2. The vector of claim 1, wherein said tetracycline-controlled activator comprises a prokaryotic tetracycline repressor fused to a transcription activation domain that activates transcription in eukaryotic cells.

3. The vector of claim 2 wherein said tetracycline-controlled activator further comprises a nuclear localization signal.

4. The vector of claim 3 wherein said transcription activation domain is derived from herpes simplex virus virion protein 16.

5. The vector of claim 3 wherein said nuclear localization signal is derived from SV40 large T antigen.

6. The vector of claim 1 wherein said promoter comprises a minimal promoter linked to at least one tetracycline operator sequence.

7. The vector of claim 6 wherein said minimal promoter is derived from a cytomegalovirus immediate early gene promoter.

8. The vector of claim 1, wherein said first cistron is positioned 5-prime of said second cistron within said transcription unit.

9. The vector of claim 1, wherein said gene product is an immunogen.

10. The vector of claim 1, wherein said gene product is a recombinant protein.

11. The vector of claim 1, wherein said gene product is selected from the group consisting of interleukin-2, tumor necrosis factor, interferon, nerve growth factor, epidermal growth factor, human growth hormone, LDL receptor, tissue plasminogen activator, Factor VIII, Factor IX, granulocyte-macrophage colony-stimulating factor, erythropoietin, insulin, calcitonin, thymidine kinase, dystrophin, and CFTR.

12. A host cell comprising the vector of claim 1.

13. A process for making the vector of claim 1 comprising
    constructing a single transcription unit and operably linking it to a tetracycline-controlled activator-responsive promoter in a plasmid backbone, said unit comprising a first cistron encoding a desired gene product and a second cistron encoding said tetracycline-controlled activator, and an internal ribosome entry site positioned between said cistrons; and
    isolating the resultant plasmid.

14. A process for inhibiting expression of the gene product in the host cell of claim 12 comprising contacting said host cell with tetracycline or a tetracycline analog, whereby expression of said gene product in said host cell is inhibited.

15. A eukaryotic expression vector in the form of VR1370 on deposit as ATCC 97467.

16. A eukaryotic expression vector based on VR1370 on deposit as ATCC 97467, modified by substitution of the CAT encoding sequence with a sequence encoding a protein of interest.

* * * * *